US009226840B2

(12) United States Patent
Augarten

(10) Patent No.: US 9,226,840 B2
(45) Date of Patent: Jan. 5, 2016

(54) MAGNETICALLY COUPLED IMPLANTABLE PUMP SYSTEM AND METHOD

(75) Inventor: Mike Augarten, Goleta, CA (US)

(73) Assignee: APOLLO ENDOSURGERY, INC., Austin, TX (US)

(*) Notice: Subject to any disclaimer, the term of this patent is extended or adjusted under 35 U.S.C. 154(b) by 502 days.

(21) Appl. No.: 12/793,566

(22) Filed: Jun. 3, 2010

(65) Prior Publication Data
US 2011/0301408 A1    Dec. 8, 2011

(51) Int. Cl.
A61F 2/00    (2006.01)
A61F 5/00    (2006.01)

(52) U.S. Cl.
CPC ............... A61F 5/0059 (2013.01); A61F 5/003 (2013.01); A61F 5/0053 (2013.01)

(58) Field of Classification Search
CPC ...... A61F 5/003; A61F 5/0059; A61F 5/0053
USPC .................. 600/9–15, 37; 604/93; 623/23.67; 606/157
See application file for complete search history.

(56) References Cited

U.S. PATENT DOCUMENTS

| | | | |
|---|---|---|---|
| 2,163,048 A | 6/1939 | McKee | |
| 3,667,081 A | 6/1972 | Burger | |
| 3,840,018 A | 10/1974 | Heifetz | |
| 4,118,805 A | 10/1978 | Reimels | |
| 4,157,713 A | 6/1979 | Clarey | |
| 4,340,083 A | 7/1982 | Cummins | |
| 4,406,656 A | 9/1983 | Hattler et al. | |
| 4,450,375 A | 5/1984 | Siegal | |
| 4,592,339 A | 6/1986 | Kuzmak | |
| 4,592,355 A | 6/1986 | Antebi | |
| 4,601,713 A | 7/1986 | Fuqua | |
| 4,671,351 A | 6/1987 | Rappe | |
| 4,696,288 A | 9/1987 | Kuzmak | |
| 4,760,837 A | 8/1988 | Petit | |
| 4,881,939 A | 11/1989 | Newman | |

(Continued)

FOREIGN PATENT DOCUMENTS

| | | |
|---|---|---|
| CN | 1250382 | 4/2000 |
| CN | 1367670 | 9/2002 |

(Continued)

OTHER PUBLICATIONS

Corno et al.; "A new implantable device for telemetric control of pulmonary blood flow," New Ideas; received Apr. 24, 2004; received in revised form Jul. 12, 2002; accepted Jul. 22, 2002.

(Continued)

Primary Examiner — Christine H Matthews
Assistant Examiner — Joshua D Lannu
(74) Attorney, Agent, or Firm — Gordon & Jacobson, P.C.

(57) ABSTRACT

A magnetically coupled, implantable pump system comprises an external controller and an implantable device. A non-implantable magnet in an external controller produces a magnetic field that couples the non-implantable magnet to a magnet in the implantable device. A non-implantable motor moves the non-implantable magnet in a rotational direction. When the non-implantable magnet moves in the rotational direction, a piston coupled to the magnet moves within the implantable device. As the piston moves, an amount of fluid from a reservoir in the implantable device moves out of the reservoir and into an inflatable portion of a gastric band. The implantable device may also move fluid out of the inflatable portion of the gastric band.

18 Claims, 3 Drawing Sheets

(56) References Cited

U.S. PATENT DOCUMENTS

| | | |
|---|---|---|
| 4,883,467 A | 11/1989 | Franetzki |
| 4,944,659 A | 7/1990 | Labbe |
| 5,045,060 A | 9/1991 | Melsky et al. |
| 5,074,868 A | 12/1991 | Kuzmak |
| 5,089,019 A | 2/1992 | Grandjean |
| 5,120,313 A | 6/1992 | Elftman |
| 5,160,338 A | 11/1992 | Vincent |
| 5,226,429 A | 7/1993 | Kuzmak |
| 5,259,399 A | 11/1993 | Brown |
| 5,326,349 A | 7/1994 | Baraff |
| 5,343,894 A | 9/1994 | Frisch et al. |
| 5,360,445 A | 11/1994 | Goldowsky |
| 5,449,368 A | 9/1995 | Kuzmak |
| 5,458,568 A | 10/1995 | Racchini et al. |
| 5,496,312 A | 3/1996 | Klicek |
| 5,535,752 A | 7/1996 | Halperin |
| 5,554,113 A | 9/1996 | Novak |
| 5,562,714 A | 10/1996 | Grevious |
| 5,601,604 A | 2/1997 | Vincent |
| 5,658,298 A | 8/1997 | Vincent et al. |
| 5,676,162 A | 10/1997 | Larson, Jr. |
| 5,733,257 A | 3/1998 | Sternby |
| 5,748,200 A | 5/1998 | Funahashi |
| 5,759,015 A | 6/1998 | Van Lintel et al. |
| 5,766,232 A | 6/1998 | Grevious |
| 5,807,311 A | 9/1998 | Palestrant |
| 5,861,014 A | 1/1999 | Familoni |
| RE36,176 E | 3/1999 | Kuzmak |
| 5,910,149 A | 6/1999 | Kuzmak |
| 5,938,669 A * | 8/1999 | Klaiber et al. .............. 606/157 |
| 6,024,340 A | 2/2000 | Lazarus et al. |
| 6,024,704 A | 2/2000 | Meador |
| 6,042,345 A | 3/2000 | Bishop et al. |
| 6,067,991 A | 5/2000 | Forsell |
| 6,074,341 A | 6/2000 | Anderson et al. |
| 6,083,249 A | 7/2000 | Familoni |
| 6,102,678 A | 8/2000 | Peclat |
| 6,102,922 A | 8/2000 | Jakobsson et al. |
| 6,164,933 A | 12/2000 | Tani et al. |
| 6,210,347 B1 | 4/2001 | Forsell |
| 6,221,024 B1 | 4/2001 | Miesel |
| 6,306,088 B1 | 10/2001 | Krausman et al. |
| 6,327,503 B1 | 12/2001 | Familoni |
| 6,409,656 B1 * | 6/2002 | Sangouard et al. ........... 600/30 |
| 6,417,750 B1 * | 7/2002 | Sohn .......................... 335/207 |
| 6,432,040 B1 | 8/2002 | Meah |
| 6,439,539 B1 | 8/2002 | Powell |
| 6,450,173 B1 | 9/2002 | Forsell |
| 6,450,946 B1 | 9/2002 | Forsell |
| 6,450,987 B1 | 9/2002 | Kramer |
| 6,453,907 B1 | 9/2002 | Forsell |
| 6,454,699 B1 | 9/2002 | Forsell |
| 6,454,700 B1 | 9/2002 | Forsell |
| 6,454,701 B1 | 9/2002 | Forsell |
| 6,454,785 B2 | 9/2002 | De Hoyas Garza |
| 6,460,543 B1 | 10/2002 | Forsell |
| 6,461,293 B1 | 10/2002 | Forsell |
| 6,463,935 B1 | 10/2002 | Forsell |
| 6,464,628 B1 | 10/2002 | Forsell |
| 6,470,892 B1 | 10/2002 | Forsell |
| 6,475,136 B1 * | 11/2002 | Forsell .......................... 600/37 |
| 6,511,490 B2 | 1/2003 | Robert |
| 6,527,701 B1 | 3/2003 | Sayet et al. |
| 6,547,801 B1 | 4/2003 | Dargent et al. |
| 6,579,301 B1 | 6/2003 | Bales et al. |
| 6,676,674 B1 | 1/2004 | Dudai |
| 6,681,135 B1 | 1/2004 | Davis et al. |
| 6,685,668 B1 | 2/2004 | Cho et al. |
| 6,691,047 B1 | 2/2004 | Fredricks |
| 6,715,731 B1 | 4/2004 | Post et al. |
| 6,729,600 B2 | 5/2004 | Mattes et al. |
| 6,754,527 B2 | 6/2004 | Stroebel et al. |
| 6,811,136 B2 | 11/2004 | Eberhardt et al. |
| 6,820,651 B2 | 11/2004 | Seuret et al. |
| 6,834,201 B2 | 12/2004 | Gillies |
| 6,871,090 B1 | 3/2005 | He |
| 6,889,086 B2 | 5/2005 | Mass et al. |
| 6,940,467 B2 | 9/2005 | Fischer |
| 6,966,875 B1 | 11/2005 | Longobardi |
| 7,017,583 B2 | 3/2006 | Forsell |
| 7,017,883 B2 | 3/2006 | Bayer et al. |
| 7,021,147 B1 | 4/2006 | Subramanian |
| 7,037,344 B2 | 5/2006 | Kagan et al. |
| 7,040,349 B2 | 5/2006 | Moler et al. |
| 7,048,519 B2 | 5/2006 | Fong et al. |
| 7,058,434 B2 | 6/2006 | Wang |
| 7,060,080 B2 | 6/2006 | Bachmann |
| 7,066,486 B2 | 6/2006 | Birk |
| 7,118,526 B2 | 10/2006 | Egle |
| 7,128,750 B1 | 10/2006 | Stergiopulos |
| 7,191,007 B2 | 3/2007 | Desai |
| 7,198,250 B2 | 4/2007 | East |
| 7,204,821 B1 | 4/2007 | Clare et al. |
| 7,206,637 B2 | 4/2007 | Salo |
| 7,238,191 B2 | 7/2007 | Bachmann |
| 7,282,023 B2 | 10/2007 | Frering |
| 7,284,966 B2 | 10/2007 | Xu et al. |
| 7,288,064 B2 | 10/2007 | Boustani et al. |
| 7,310,557 B2 | 12/2007 | Maschino et al. |
| 7,311,503 B2 | 12/2007 | Van Lintel et al. |
| 7,311,716 B2 | 12/2007 | Byrum |
| 7,311,717 B2 | 12/2007 | Egle |
| 7,314,443 B2 | 1/2008 | Jordan et al. |
| 7,338,433 B2 | 3/2008 | Coe |
| 7,351,198 B2 | 4/2008 | Byrum |
| 7,351,240 B2 | 4/2008 | Hassler |
| 7,353,747 B2 | 4/2008 | Swayze et al. |
| 7,364,542 B2 | 4/2008 | Jambor et al. |
| 7,366,571 B2 | 4/2008 | Armstrong |
| 7,367,340 B2 | 5/2008 | Nelson |
| 7,367,937 B2 | 5/2008 | Jambor |
| 7,374,565 B2 | 5/2008 | Hassler, Jr. |
| 7,390,294 B2 | 6/2008 | Hassler |
| 7,396,353 B2 | 7/2008 | Lorenzen |
| 7,416,528 B2 | 8/2008 | Crawford et al. |
| 7,481,763 B2 | 1/2009 | Hassler |
| 7,500,944 B2 | 3/2009 | Byrum |
| 7,530,943 B2 | 5/2009 | Lechner |
| 7,594,885 B2 | 9/2009 | Byrum |
| 7,599,743 B2 | 10/2009 | Hassler |
| 7,599,744 B2 | 10/2009 | Giordano |
| 7,601,162 B2 | 10/2009 | Hassler, Jr. et al. |
| 7,615,001 B2 | 11/2009 | Jambor |
| 7,618,365 B2 | 11/2009 | Jambor |
| 7,658,196 B2 | 2/2010 | Ferreri |
| 7,699,770 B2 | 4/2010 | Hassler |
| 7,727,141 B2 | 6/2010 | Hassler, Jr. et al. |
| 7,758,493 B2 | 7/2010 | Gingras |
| 7,766,815 B2 | 8/2010 | Ortiz |
| 7,771,439 B2 | 8/2010 | Griffiths |
| 7,775,215 B2 | 8/2010 | Hassler, Jr. et al. |
| 7,775,966 B2 | 8/2010 | Dlugos et al. |
| 7,794,386 B2 | 9/2010 | Brooks |
| 7,811,298 B2 | 10/2010 | Birk |
| 7,844,342 B2 | 11/2010 | Dlugos et al. |
| 2001/0011543 A1 | 8/2001 | Forsell |
| 2002/0072780 A1 | 6/2002 | Foley |
| 2002/0091395 A1 | 7/2002 | Gabbay |
| 2002/0095181 A1 | 7/2002 | Beyar |
| 2002/0139208 A1 | 10/2002 | Yatskov |
| 2002/0193679 A1 | 12/2002 | Malave et al. |
| 2002/0198548 A1 | 12/2002 | Robert |
| 2003/0019498 A1 | 1/2003 | Forsell |
| 2003/0045775 A1 | 3/2003 | Forsell |
| 2003/0055311 A1 | 3/2003 | Neukermans et al. |
| 2003/0066536 A1 | 4/2003 | Forsell |
| 2003/0073880 A1 | 4/2003 | Polsky et al. |
| 2003/0158569 A1 | 8/2003 | Wazne |
| 2003/0191433 A1 | 10/2003 | Prentiss |
| 2003/0208212 A1 | 11/2003 | Cigaina |

(56) References Cited

U.S. PATENT DOCUMENTS

| | | |
|---|---|---|
| 2004/0000843 A1 | 1/2004 | East |
| 2004/0044332 A1 | 3/2004 | Stergiopulos |
| 2004/0059393 A1 | 3/2004 | Policker et al. |
| 2004/0133219 A1 | 7/2004 | Forsell |
| 2004/0147816 A1 | 7/2004 | Policker et al. |
| 2004/0148034 A1 | 7/2004 | Kagan et al. |
| 2004/0153106 A1 | 8/2004 | Dudai |
| 2004/0162595 A1 | 8/2004 | Foley |
| 2004/0215159 A1 | 10/2004 | Forsell |
| 2004/0230137 A1 | 11/2004 | Mouton |
| 2004/0254536 A1 | 12/2004 | Conlon et al. |
| 2004/0254537 A1 | 12/2004 | Conlon et al. |
| 2004/0260319 A1 | 12/2004 | Egle |
| 2004/0267288 A1 | 12/2004 | Byrum |
| 2004/0267291 A1 | 12/2004 | Byrum et al. |
| 2004/0267292 A1 | 12/2004 | Byrum |
| 2004/0267293 A1 | 12/2004 | Byrum et al. |
| 2004/0267377 A1 | 12/2004 | Egle |
| 2005/0002984 A1 | 1/2005 | Byrum |
| 2005/0038484 A1 | 2/2005 | Knudson et al. |
| 2005/0055039 A1 | 3/2005 | Burnett et al. |
| 2005/0070934 A1 | 3/2005 | Tanaka et al. |
| 2005/0070937 A1 | 3/2005 | Jambor |
| 2005/0104457 A1 | 5/2005 | Jordan et al. |
| 2005/0119672 A1 | 6/2005 | Benchetrit |
| 2005/0119674 A1 | 6/2005 | Gingras |
| 2005/0131383 A1 | 6/2005 | Chen et al. |
| 2005/0131485 A1 | 6/2005 | Knudson et al. |
| 2005/0143765 A1 | 6/2005 | Bachmann et al. |
| 2005/0143766 A1 | 6/2005 | Bachmann et al. |
| 2005/0183730 A1 | 8/2005 | Byrum |
| 2005/0192531 A1 | 9/2005 | Birk |
| 2005/0192601 A1 | 9/2005 | Demarais |
| 2005/0192614 A1 | 9/2005 | Binmoeller |
| 2005/0216042 A1 | 9/2005 | Gertner |
| 2005/0228415 A1 | 10/2005 | Gertner |
| 2005/0240155 A1 | 10/2005 | Conlon |
| 2005/0240156 A1 | 10/2005 | Conlon |
| 2005/0240279 A1 | 10/2005 | Kagan et al. |
| 2005/0244288 A1 | 11/2005 | O'Neill |
| 2005/0250979 A1 | 11/2005 | Coe |
| 2005/0251181 A1 | 11/2005 | Bachmann |
| 2005/0251182 A1 | 11/2005 | Bachmann |
| 2005/0267406 A1 | 12/2005 | Hassler |
| 2005/0267500 A1 | 12/2005 | Hassler et al. |
| 2005/0267533 A1 | 12/2005 | Gertner |
| 2005/0277899 A1 | 12/2005 | Conlon et al. |
| 2005/0283041 A1 | 12/2005 | Egle |
| 2005/0288739 A1 | 12/2005 | Hassler |
| 2005/0288740 A1 | 12/2005 | Hassler |
| 2006/0041183 A1 | 2/2006 | Massen et al. |
| 2006/0074439 A1 | 4/2006 | Garner et al. |
| 2006/0074473 A1 | 4/2006 | Gertner |
| 2006/0089571 A1 | 4/2006 | Gertner |
| 2006/0161186 A1 | 7/2006 | Hassler et al. |
| 2006/0173238 A1 | 8/2006 | Starkebaum |
| 2006/0173424 A1 | 8/2006 | Conlon |
| 2006/0178555 A1 | 8/2006 | Bortolotti |
| 2006/0183967 A1 | 8/2006 | Lechner |
| 2006/0189887 A1 | 8/2006 | Hassler |
| 2006/0189888 A1 | 8/2006 | Hassler |
| 2006/0189889 A1 | 8/2006 | Gertner |
| 2006/0195139 A1 | 8/2006 | Gertner |
| 2006/0197412 A1 | 9/2006 | Rasmussen |
| 2006/0199997 A1 | 9/2006 | Hassler |
| 2006/0211912 A1 | 9/2006 | Dlugos |
| 2006/0211913 A1 | 9/2006 | Dlugos |
| 2006/0211914 A1 | 9/2006 | Hassler |
| 2006/0212053 A1 | 9/2006 | Gertner |
| 2006/0235448 A1 | 10/2006 | Roslin et al. |
| 2006/0247722 A1 | 11/2006 | Maschino et al. |
| 2006/0247724 A1 | 11/2006 | Gerber et al. |
| 2006/0252982 A1 | 11/2006 | Hassler, Jr. et al. |
| 2006/0264699 A1 | 11/2006 | Gertner |
| 2006/0276812 A1 | 12/2006 | Hill et al. |
| 2007/0015954 A1 | 1/2007 | Dlugos |
| 2007/0015955 A1 | 1/2007 | Tsonton |
| 2007/0016262 A1 | 1/2007 | Gross et al. |
| 2007/0027356 A1 | 2/2007 | Ortiz |
| 2007/0078476 A1 | 4/2007 | Hull et al. |
| 2007/0125826 A1 | 6/2007 | Shelton |
| 2007/0156013 A1 | 7/2007 | Birk |
| 2007/0167672 A1 | 7/2007 | Dlugos et al. |
| 2007/0185462 A1 | 8/2007 | Byrum |
| 2007/0218083 A1 | 9/2007 | Brooks |
| 2007/0232848 A1 | 10/2007 | Forsell |
| 2007/0235083 A1 | 10/2007 | Dlugos |
| 2007/0250085 A1 | 10/2007 | Bachmann et al. |
| 2007/0250086 A1 | 10/2007 | Wiley |
| 2007/0255336 A1 | 11/2007 | Herbert et al. |
| 2007/0265598 A1 | 11/2007 | Karasik |
| 2007/0265645 A1 | 11/2007 | Birk et al. |
| 2008/0009680 A1 | 1/2008 | Hassler |
| 2008/0015406 A1 | 1/2008 | Dlugos |
| 2008/0027469 A1 | 1/2008 | Bachmann |
| 2008/0097496 A1 | 4/2008 | Chang et al. |
| 2008/0108862 A1 | 5/2008 | Jordan et al. |
| 2008/0166028 A1 | 7/2008 | Turek et al. |
| 2008/0221598 A1 | 9/2008 | Dlugos |
| 2008/0249806 A1 | 10/2008 | Dlugos |
| 2008/0250340 A1 | 10/2008 | Dlugos |
| 2008/0250341 A1 | 10/2008 | Dlugos |
| 2008/0255403 A1 | 10/2008 | Voegele et al. |
| 2008/0255414 A1 | 10/2008 | Voegele et al. |
| 2008/0255425 A1 | 10/2008 | Voegele et al. |
| 2008/0255459 A1 | 10/2008 | Voegele et al. |
| 2008/0255537 A1 | 10/2008 | Voegele et al. |
| 2008/0287969 A1 | 11/2008 | Tsonton et al. |
| 2008/0287974 A1 | 11/2008 | Widenhouse et al. |
| 2008/0287976 A1 | 11/2008 | Weaner et al. |
| 2008/0319435 A1 | 12/2008 | Rioux et al. |
| 2009/0054914 A1 | 2/2009 | Lechner |
| 2009/0062825 A1* | 3/2009 | Pool et al. .................. 606/157 |
| 2009/0062826 A1 | 3/2009 | Steffen |
| 2009/0082793 A1 | 3/2009 | Birk |
| 2009/0118572 A1 | 5/2009 | Lechner |
| 2009/0157106 A1 | 6/2009 | Marcotte |
| 2009/0157107 A1 | 6/2009 | Kierath et al. |
| 2009/0157113 A1 | 6/2009 | Marcotte et al. |
| 2009/0171375 A1 | 7/2009 | Coe et al. |
| 2009/0171378 A1* | 7/2009 | Coe et al. .................. 606/157 |
| 2009/0171379 A1 | 7/2009 | Coe et al. |
| 2009/0192404 A1 | 7/2009 | Ortiz |
| 2009/0192415 A1 | 7/2009 | Ortiz et al. |
| 2009/0192533 A1 | 7/2009 | Dlugos, Jr. et al. |
| 2009/0192534 A1 | 7/2009 | Ortiz et al. |
| 2009/0192541 A1 | 7/2009 | Ortiz et al. |
| 2009/0198261 A1 | 8/2009 | Schweikert |
| 2009/0202387 A1 | 8/2009 | Dlugos, Jr. et al. |
| 2009/0204131 A1 | 8/2009 | Ortiz |
| 2009/0204132 A1 | 8/2009 | Ortiz |
| 2009/0204141 A1 | 8/2009 | Dlugos, Jr. et al. |
| 2009/0204179 A1 | 8/2009 | Dlugos, Jr. et al. |
| 2009/0209995 A1 | 8/2009 | Byrum et al. |
| 2009/0216255 A1 | 8/2009 | Coe et al. |
| 2009/0222031 A1 | 9/2009 | Axelsson |
| 2009/0222065 A1 | 9/2009 | Dlugos, Jr. et al. |
| 2009/0228072 A1 | 9/2009 | Coe et al. |
| 2009/0270904 A1 | 10/2009 | Birk et al. |
| 2009/0306462 A1 | 12/2009 | Lechner |
| 2009/0312785 A1 | 12/2009 | Stone et al. |
| 2010/0010291 A1 | 1/2010 | Birk |
| 2010/0087843 A1 | 4/2010 | Bertolote et al. |
| 2010/0099945 A1 | 4/2010 | Birk et al. |
| 2010/0100079 A1 | 4/2010 | Berkcan |
| 2010/0152532 A1 | 6/2010 | Marcotte |
| 2010/0185049 A1 | 7/2010 | Birk et al. |
| 2010/0191271 A1 | 7/2010 | Lau et al. |
| 2010/0228080 A1 | 9/2010 | Tavori et al. |
| 2010/0249803 A1 | 9/2010 | Griffiths |

(56) References Cited

U.S. PATENT DOCUMENTS

| | | |
|---|---|---|
| 2010/0280310 A1 | 11/2010 | Raven |
| 2010/0305397 A1 | 12/2010 | Birk et al. |
| 2010/0324358 A1 | 12/2010 | Birk et al. |
| 2010/0324359 A1 | 12/2010 | Birk |

FOREIGN PATENT DOCUMENTS

| | | |
|---|---|---|
| DE | 4225524 | 2/1994 |
| DE | 10020688 | 12/2000 |
| EP | 0119596 | 9/1984 |
| EP | 0230747 | 8/1987 |
| EP | 0611561 | 8/1994 |
| EP | 0695558 | 2/1996 |
| EP | 0867808 | 11/1998 |
| EP | 1072282 | 1/2001 |
| EP | 1396242 | 3/2004 |
| EP | 1396243 | 3/2004 |
| EP | 1491167 | 12/2004 |
| EP | 1547549 | 6/2005 |
| EP | 1600183 | 11/2005 |
| EP | 1602346 | 12/2005 |
| EP | 1704833 | 9/2006 |
| EP | 1719480 | 11/2006 |
| EP | 1754890 | 11/2006 |
| EP | 1736123 | 12/2006 |
| EP | 2074970 | 7/2009 |
| EP | 2074971 | 7/2009 |
| EP | 2087862 | 8/2009 |
| EP | 2095796 | 9/2009 |
| EP | 2095798 | 9/2009 |
| FR | 2797181 | 2/2001 |
| FR | 2823663 | 10/2002 |
| FR | 2855744 | 12/2004 |
| FR | 2921822 | 4/2009 |
| JP | 2005-334658 | 12/2005 |
| WO | WO 89/11701 | 11/1989 |
| WO | WO 00/09047 | 2/2000 |
| WO | WO 00/09048 | 2/2000 |
| WO | WO 00/09049 | 2/2000 |
| WO | WO 00/15158 | 3/2000 |
| WO | WO 00/66196 | 11/2000 |
| WO | WO 01/10359 | 2/2001 |
| WO | WO 01/12078 | 2/2001 |
| WO | WO 01/47575 | 7/2001 |
| WO | WO 01/49245 | 7/2001 |
| WO | WO 01/70131 | 9/2001 |
| WO | WO 02/26317 | 4/2002 |
| WO | WO 02/053093 | 7/2002 |
| WO | WO 02/065948 | 8/2002 |
| WO | WO 03/077191 | 9/2003 |
| WO | WO 03/105732 | 12/2003 |
| WO | WO 2004/014245 | 2/2004 |
| WO | WO 2004/019671 | 3/2004 |
| WO | WO 2005/007232 | 1/2005 |
| WO | WO 2005/009305 | 2/2005 |
| WO | WO 2005/087147 | 9/2005 |
| WO | WO 2005/094447 | 10/2005 |
| WO | WO 2006/083885 | 8/2006 |
| WO | WO 2006/108203 | 10/2006 |
| WO | WO 2008/109300 | 9/2008 |
| WO | WO 2009/132127 | 10/2009 |

OTHER PUBLICATIONS

"Innovative medical devices and implants," LGSP Medical futures, p. 5.

Corno et al.; "FloWatchTM in clipped and inclipped position," Interact Cardio Vase Thorac Surg 2002; 1:46-49.

BioEnterics Lap-Band Adjustable Gastric Banding System, Inamed Health, pub. Aug. 28, 2003 pp. 1-115.

Iverson et al.; "Recent Advances in Microscale Pumping Technologies: A Review and Evaluation"; Microfluid Nanofluid; vol. 5; pp. 145-174; Feb. 19, 2008.

* cited by examiner

MAGNETICALLY COUPLED IMPLANTABLE PUMP SYSTEM AND METHOD

FIELD

The present invention generally relates to medical systems and apparatus and uses thereof for treating obesity and/or obesity-related diseases, and more specifically, relates to implantable pump systems that are remotely actuated by a magnetic coupling with an external device.

BACKGROUND

Adjustable gastric banding apparatus have provided an effective and substantially less invasive alternative to gastric bypass surgery and other conventional surgical weight loss procedures. Despite the positive outcomes of invasive weight loss procedures, such as gastric bypass surgery, it has been recognized that sustained weight loss can be achieved through a laparoscopically-placed gastric band, for example, the LAP-BAND® (Allergan, Inc., Irvine, Calif.) gastric band or the LAP-BAND AP® (Allergan, Inc., Irvine, Calif.) gastric band. Generally, gastric bands are placed about the cardia, or upper portion, of a patient's stomach forming a stoma that restricts the passage of food into a lower portion of the stomach. When the stoma is of an appropriate size that is restricted by a gastric band, food held in the upper portion of the stomach provides a feeling of satiety or fullness that discourages overeating. Unlike gastric bypass procedures, the gastric band apparatus are reversible and require no permanent modification to the gastrointestinal tract.

Over time, a stoma created by a gastric band may need adjustment in order to maintain an appropriate size, which is neither too restrictive nor too passive. Accordingly, prior art gastric band systems provide a subcutaneous fluid access port connected to an expandable or inflatable portion of the gastric band. By adding fluid to or removing fluid from the inflatable portion by means of a hypodermic needle inserted into the access port, the effective size of the gastric band can be adjusted to provide a tighter or looser constriction.

Some non-invasive procedures for adjustment of gastric bands without the use of a hypodermic needle have been proposed. For example, a remotely adjustable gastric band is a medical device which allows a healthcare worker to adjust a gastric band without requiring hypodermic needles to connect to an implanted, subcutaneous access port. A handheld controller can be used to send radio frequency waves for powering and communicating with the implanted device. The implanted device can fill or drain the gastric band as requested by the healthcare worker via the handheld controller.

Such remotely adjustable gastric band systems have some challenges. For example, the implantable pump system has certain design parameters relating to size, power dissipation, flow rate, back pressure, and Magnetic Resonance Imaging (MRI) considerations. These different parameters result in sometimes conflicting constraints for the pump implementation.

Some remotely adjustable pump motors may be powered by a piezo element in a peristaltic pump. In certain circumstances, actuation of the piezo element (or combination of piezo elements) may result in heating of the patient's tissue.

Some other implantable devices have also been disclosed, but these devices suffer from certain disadvantages. For example, Sohn, U.S. Pat. No. 6,417,750, generally discloses magnetically-coupled implantable medical devices, but Sohn does not disclose implantable pumps for use with gastric banding systems.

Hassler, et al., U.S. Pat. No. 7,390,294, discloses a bellows accumulator driven by a piezoelectric system. The system collapses or extends to displace accumulated fluid. The system serves as both a reversible pump and reservoir. However, Hassler utilizes internal electrical power to drive the pump, which may lead to heating of a patient's tissue.

Lorenzen, et al., U.S. Pat. No. 7,396,353, discloses an infusion device and a driving mechanism for delivery of an infusion medium. A coil capable of being electrically activated to provide an electromagnetic field surrounds a piston channel. The piston channel provides a passage for communication of the infusion medium to an outlet chamber located at one end of the piston channel. Because the coil utilizes energy local to the drive mechanism in order to deliver the infusion medium, Lorenzen's device may also lead to heating of a patient's tissue.

Gillies, U.S. Pat. No. 6,834,201, discloses catheter navigation using an MRI device. The internal device utilizes coils that are responsive to an external magnetic field. The current induced in the internal coils generates heat that is then dissipated, so Gillies requires additional components in order to attempt to dissipate the generated heat.

Nelson, et al., U.S. Pat. No. 7,367,340, discloses systems and methods for moving and/or restraining tissue in the upper respiratory system of a patient. But Nelson does not disclose driving an internal magnet with an external magnet. In fact, all of Nelson's magnets are internal. Further, Nelson does not disclose driving a pump to fill or drain an inflatable portion of a gastric band.

Some remotely adjustable gastric banding systems that have been proposed utilize external power and/or transmit telemetric signals through the skin in order to power and/or actuate pumps associated with the remotely adjustable systems. Thus, remotely adjustable gastric banding systems that receive less or no power from an external transmitter are disclosed herein. Further, remotely adjustable gastric banding systems that reduce tissue heating are disclosed herein.

SUMMARY

Generally described herein are remotely adjustable and remotely powered gastric band systems, and methods of use thereof. The apparatus, systems and methods described herein aid in facilitating obesity control and/or treating obesity-related diseases while being non-invasive once implanted.

In an embodiment, a system for adjusting a gastric band comprises an external controller and an implantable device. The external controller comprises a non-implantable magnet that produces a magnetic field. The external controller also comprises a non-implantable motor that is coupled to the non-implantable magnet. The non-implantable motor moves the non-implantable magnet in a rotational direction.

The implantable device comprises a magnet that is magnetically coupled to the non-implantable magnet. A piston is coupled to the magnet and is located next to a reservoir that contains a fluid. The implantable device may comprise a screw drive coupled between the magnet and the piston to facilitate moving the piston within the implantable device. In an embodiment, the implantable device comprises a seal to prevent leakage of the fluid in the reservoir. Further, in an embodiment, the reservoir may be located within a flexible pouch disposed in the implantable device.

The gastric band has an inflatable portion that may be filled or drained with the implantable device. For example, when the magnet rotates in response to the rotation of the non-implantable magnet, the piston moves within the implantable device causing a portion of the fluid in the reservoir to move into the inflatable portion of the gastric band. The magnet may also rotate in a second direction to facilitate draining the inflatable portion of the gastric band.

A method for adjusting the inflatable portion of the gastric band comprises positioning the external controller near a patient. A magnetic field is generated by the non-implantable magnet, which causes the non-implantable magnet to be magnetically coupled to the magnet of the implantable device. The non-implantable magnet moves in a first direction which causes the magnet to also move in the first direction. A first portion of the fluid in the reservoir moves into the inflatable portion of the gastric band when the magnet moves in the first direction. The non-implantable magnet may also be moved in a second direction which causes the magnet to also move in the second direction. A second portion of the fluid from the inflatable portion of the gastric band moves into the reservoir when the magnet moves in the second direction.

In an alternate embodiment, a system for adjusting a gastric band with an inflatable portion comprises a non-implanted, rotatable magnet capable of producing a magnetic field. The system further includes an implantable device that comprises a reservoir containing a fluid and coupled to the inflatable portion of the gastric band. A second magnet is magnetically coupled to the non-implanted magnet, and the second magnet rotates in response to the non-implanted magnet rotating. The implantable device also comprises a piston coupled to the second magnet, and the piston moves in response to the second magnet rotating. When the piston moves, a portion of the fluid in the reservoir moves into or out of the inflatable portion of the gastric band.

Further, in another embodiment, an implantable system for adjusting a gastric band implanted in a patient for a treatment of obesity comprises a reservoir containing a fluid. The reservoir is coupled to an inflatable portion of the gastric band. An internal magnet is magnetically coupled to a magnet external to the patient, and the internal magnet moves in response to the external magnet moving. The implantable system also includes a piston coupled to the internal magnet. The piston moves in response to the internal magnet moving, thereby causing a portion of the fluid in the reservoir to move into or out of the inflatable portion of the gastric band.

DETAILED DESCRIPTION

Figure 1:
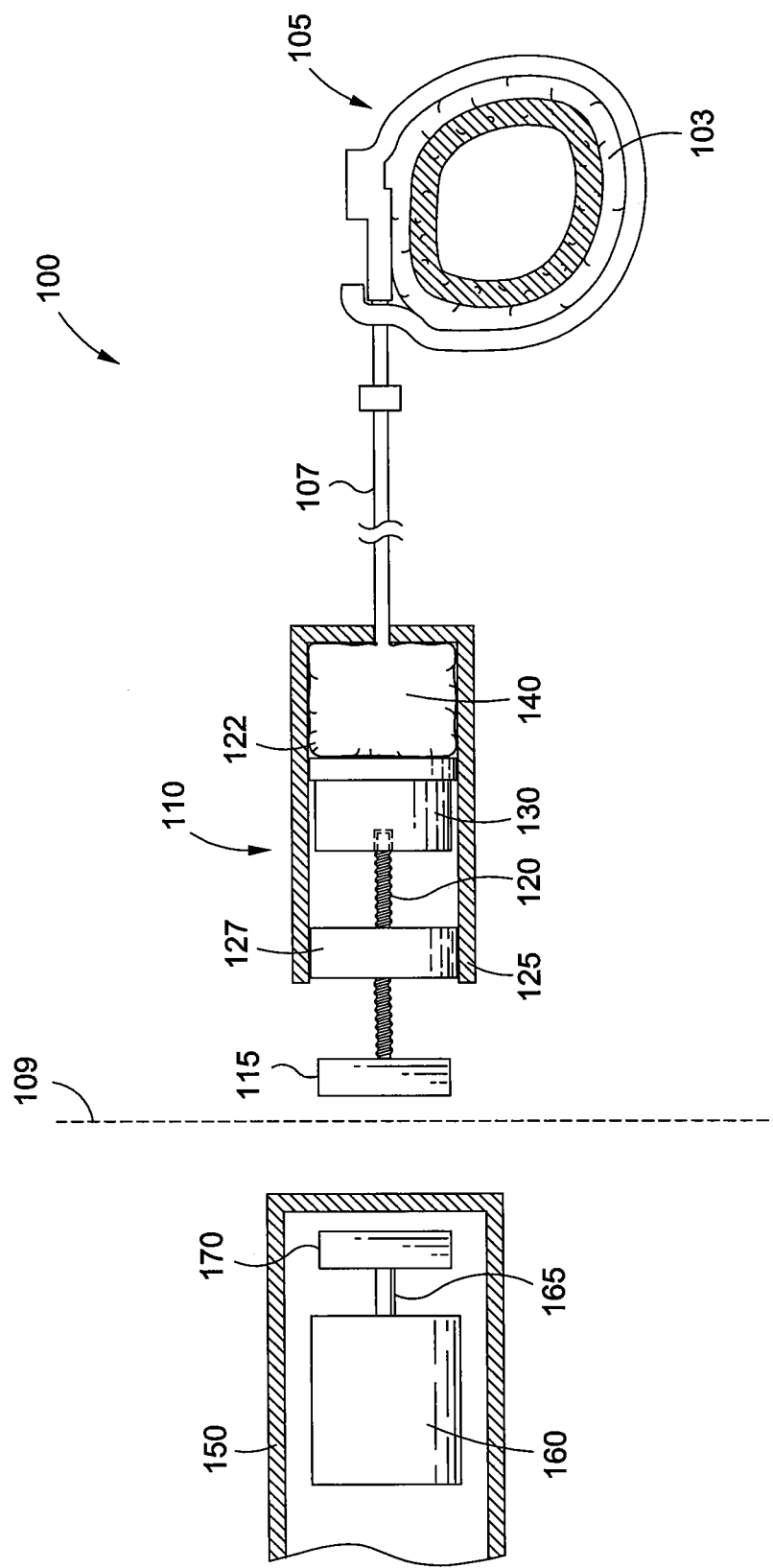
FIG. 1 illustrates a side, sectional view of a gastric banding system and an external controller according to an embodiment of the present invention.

The present invention generally provides remotely adjustable gastric banding systems, for example, for treatment of obesity and obesity related conditions, as well as systems for controlling inflation of gastric banding systems.

A remotely adjustable gastric band is a medical device which allows a healthcare worker to adjust a gastric band without utilizing hypodermic needles to connect to an implanted access port. An external and/or handheld controller can be used to cause the implanted device to fill or drain the gastric band as requested by the healthcare worker via the handheld controller. The handheld controller may be a remote device configured to communicate with the implantable device using a magnetic and/or electrical field.

The filling and draining of the band is accomplished by a set of fluidic elements including pumps, valves, and sensors which monitor and/or move fluid between the gastric band and a reservoir. In accordance with various embodiments, different numbers, types, and orientations of the fluidic elements may be utilized to obtain the desired results. Any and/or all of these various components may be configured to be controlled by an external controller.

The fluids used within the systems of the present invention include any fluid that is biocompatible and incompressible. The fluid has no adverse effect on the patient in the unlikely event that a leak emanates from the system. The fluid can simply be water or any biocompatible polymer oil such as castor oil. In an example embodiment, the fluid is saline.

In various embodiments, motion in the external controller may induce motion in the implantable device to move fluid into or out of an inflatable portion of the gastric band. For example, the external controller may include a rotational motor that causes an external magnet within and/or proximate to the external controller to rotate. In an alternate embodiment, a motor may not be utilized to cause the external magnet to rotate. Rather, the external magnet may be rotated manually and/or by other means. Any system that allows adjustment of a gastric banding system by moving a magnet external to the patient's body is contemplated within the scope of the present invention.

The external magnet is magnetically coupled to a magnet in the implantable device, and when the external magnet rotates, the internal magnet rotates as well. The internal rotational magnet may be connected to a pump directly or may provide torque transfer via a spring, gears, or similar implementation to a suitable pump mechanism. The external controller may further include a linear motor that causes an external magnet to move in a linear direction to induce linear motion in an internal magnet to actuate the pump.

In various embodiments, different pumps may be utilized to provide a motion that moves the fluid from the pump to the gastric band. For example, rotary motion actuators, linear geared actuators, mechanical pumps, stroke pumps, geared plungers, and combinations thereof may be utilized to provide the desired pumping action.

With reference to FIG. 1, one embodiment of the invention comprises an internal gastric banding system 100 and an external controller 150. The external controller 150 may comprise a motor 160 which may be referred to as a non-implantable motor because of its location external to a patient's body. The motor 160 is coupled to a rotational magnet 170 that is also external to the patient's body. The rotational magnet 170 may also be referred to as a non-implantable magnet because it is not implanted in the patient's body. As noted above, a motor may not be used to rotate the rotational magnet 170. Rather, manual and other means may be utilized to rotate the rotational magnet 170.

The rotational magnet 170 is coupled to the motor 160 via a drive shaft 165 that facilitates rotation of the rotational magnet 170. The motor 160, the driveshaft 165, and/or the rotational magnet 170 may be located within and/or outside of the handheld controller 150. For example, the rotational magnet 170 may be located at least partially outside of the controller 150.

The internal gastric banding system 100 comprises an implantable device, such as an implantable pump 110 that is coupled to a gastric band 105 via tubing 107. The implantable pump 110 is operable to move a fluid between the pump 110 and an inflatable portion 103 of the gastric band 105 to facilitate adjustment of the gastric band 105 about the patient's stomach.

According to various embodiments, components of the gastric banding system 100 may be placed in their respective positions within a patient using common surgical techniques. The surgical techniques may be similar to those used in the placement of conventional gastric banding systems. For example, the gastric band 105 may be placed around the stomach using laparoscopic techniques, as known to those of skill in the art. Like a conventional access port, various components of the gastric banding system 100 may be sutured onto the rectus muscle sheath or any other conveniently accessible muscle. The tubing 107 to the gastric band 105 passes through the rectus muscle into the peritoneal cavity in the same or similar manner as the tubing of a conventional access port.

The implantable pump 110 may be used to replace or complement a conventional access port for adjusting inflation of the gastric band 105. In some embodiments, the system includes a conventional access port fluidly coupled to the gastric banding system 100, for example, between a reservoir 140 and a piston 130. The conventional access port may also be coupled to the tubing 107, directly to the gastric band 105, and/or to other components of the gastric banding system 100 in order to fill and drain the inflatable portion 103 of the gastric band 105. The conventional access port may be used, for example, with a hypodermic needle via a subcutaneous injection, to fill or drain the gastric band 105 in conjunction with and/or in addition to the filling and draining provided by the implantable pump 110.

In an embodiment, the pump 110 comprises the piston 130 that acts on the fluid contained in the syringe-type reservoir 140. As the piston 130 moves within a housing 125 of the pump 110, the piston 130 causes the fluid to enter or exit the reservoir 140 in order to fill or drain the inflatable portion 103 of the gastric band 105. A flow meter and/or flow control device may be coupled between the reservoir 140 and the gastric band 105 to measure the amount of the fluid moving into or out of the inflatable portion 103 of the gastric band 105. The fluid may be contained within a pouch 122 that is coupled to the tubing 107 to facilitate filling or draining the gastric band 105. In an embodiment, a seal may be utilized between the piston 130, the housing 125 and/or the reservoir 140 in order to prevent leakage of the fluid from the reservoir 140.

The reservoir 140 and the piston 130 may move precisely metered volumes of a fluid (e.g., saline) through the tubing 107 into the gastric band 105. Moving the fluid into the gastric band 105 causes inflation of the inflatable portion 103, such as at least one bladder, and constricts around the cardia, or upper portion of the stomach, forming a stoma that restricts the passage of food into a lower portion of the stomach. This stoma can provide a patient with a sensation of satiety or fullness that discourages overeating.

In contrast, moving the fluid out of the inflatable portion 103 of the gastric band 105 contracts the pressure around the cardia and allows a stoma to be at least partially released and regains the patient's hunger sensation. The reservoir 140 and the piston 130 facilitate moving the fluid out of the gastric band 105.

In an embodiment, the piston 130 is coupled to an internal magnet 115 via an internal drive shaft 120. For example, as illustrated in FIG. 1, the internal drive shaft 120 may include a screw drive. The drive shaft 120 is coupled to a header 127 disposed between the piston 130 and the internal magnet 115 such that the magnet 115 and the piston 130 move in a direction normal to the header 127 when the magnet 115 rotates. Similarly, when the magnet 115 rotates, the piston 130 moves in an axial direction within the pump 110 in order to move fluid into or out of the reservoir 140. For example, the magnet 115 may move clockwise for reduction of the volume in the reservoir 140, and the magnet 115 may move counterclockwise for expansion of the volume in the reservoir 140.

Figure 2:
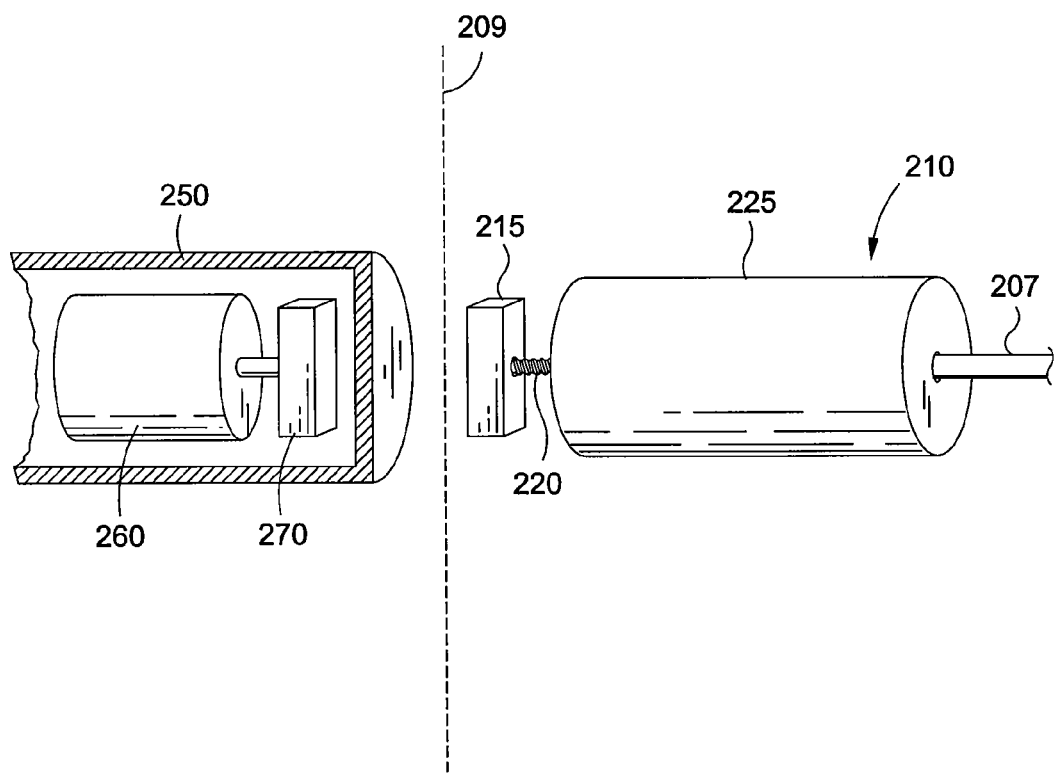
FIG. 2 illustrates a perspective view of a gastric banding system and an external controller according to an embodiment of the present invention.

In an embodiment, as illustrated in FIG. 2, an implantable pump 210 is implanted within a patient's body. A boundary 209, such as skin, separates the implantable pump 210 from the external controller 250. When the external controller 250 is brought sufficiently close to the boundary 209 and/or the internal magnet 215, an external magnet 270 within the external controller 250 magnetically couples to the internal magnet 215.

A motor 260 in the external controller 250 causes the external magnet 270 to rotate, and the magnetic field that permeates the boundary 209 causes the internal magnet 215 to rotate. As the internal magnet 215 rotates turning drive shaft 220, fluid enters or exits the implantable pump 225 of system 210 via tubing 207 in order to fill or drain the gastric band.

In such a configuration, the power for the pump 210 may be provided solely through the magnetic coupling, and the pump 210 would not utilize any internal electric power. The electric power is provide externally, with respect to the patient, in order to drive the rotation of the external magnet 270.

Thus, embodiments of the present invention allow for the filling and draining the gastric band while minimizing power dissipation within the implantable pump 210, which reduces the resultant temperature rise of the patient's tissue surrounding the pump 210. In various embodiments, a substantial amount of power is moved from within the patient's body to the external controller 250 where enhanced power generation and cooling methods may be implemented.

The physical separation distance between the external magnet 270 and the internal magnet 215 is advantageously determined to provide a magnetic field of sufficient strength to rotate the magnet 215 and move fluid into or out of the pump 210. For example, in an embodiment, the external magnet 270 may be located within approximately 5-10 centimeters of the internal magnet 215. In other embodiments, where stronger or weaker magnets are used, the operational distance between the two magnets may be selected from the range of approximately 1-15 centimeters. It should be understood that any type of magnet that facilitates magnetic coupling of the external magnet 270 to the internal magnet 215 in order to move fluid into or out of the pump 210 is contemplated within the scope of the present invention.

In accordance with various embodiments, the pump 210 disclosed herein provides advantages over other existing pumps for gastric banding systems that utilize inductive powering to drive pumps to fill and drain a gastric band. Such existing systems require internal electrical power to drive these internal pumps (e.g., piezoelectric pumps), and these pumps may be subject to low flow rates. With internal electrical power, the pumps may heat up more and dissipate more heat within the patient. In an embodiment of the present invention, inductive powering is not required to power the pump 210, because the internal magnet 215 and the external magnet 270 are utilized to drive the pump 210. Thus, the high power portion of a previous implantable pump system is moved to the outside of the patient's body, which reduces heating of the patient's tissue.

Embodiments of the present invention are more compact and efficient than existing gastric banding systems that use non-invasive adjustment methods. For example, the implantable device 210 may have a smaller overall size as compared to implementations using other internally powered pump methods, because the implantable device 210 does not need to accommodate space for an internal motor.

Figure 3:
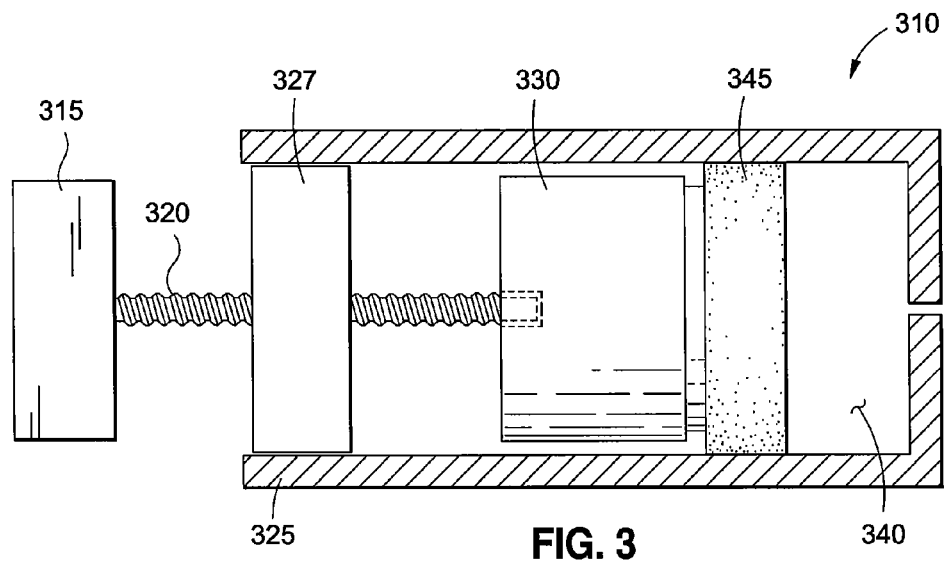
FIG. 3 illustrates a side, sectional view of an implantable pump with a seal according to an embodiment of the present invention.

Turning now to FIG. 3, one embodiment of a pump 310 includes internal magnet 315 connected to drive shaft 320 and a slidable seal 345 disposed between a reservoir 340 and a piston 330. The drive shaft 320 is connected to header 327. The seal 345 facilitates hermetically sealing the reservoir 340 such that the fluid does not leak from the reservoir 340. The seal 345 maintains a sufficient contact with a housing 325 of the pump 310 in order to prevent leakage of the fluid from the reservoir 340 into the pump 310. This contact creates friction with the housing 325 which results in a resistance to movement of the piston 330 within the pump 310. Thus, sufficient force may need to be applied to move the piston 330 and the seal 345 in order to modify the amount of fluid in the reservoir 340.

Figure 4:
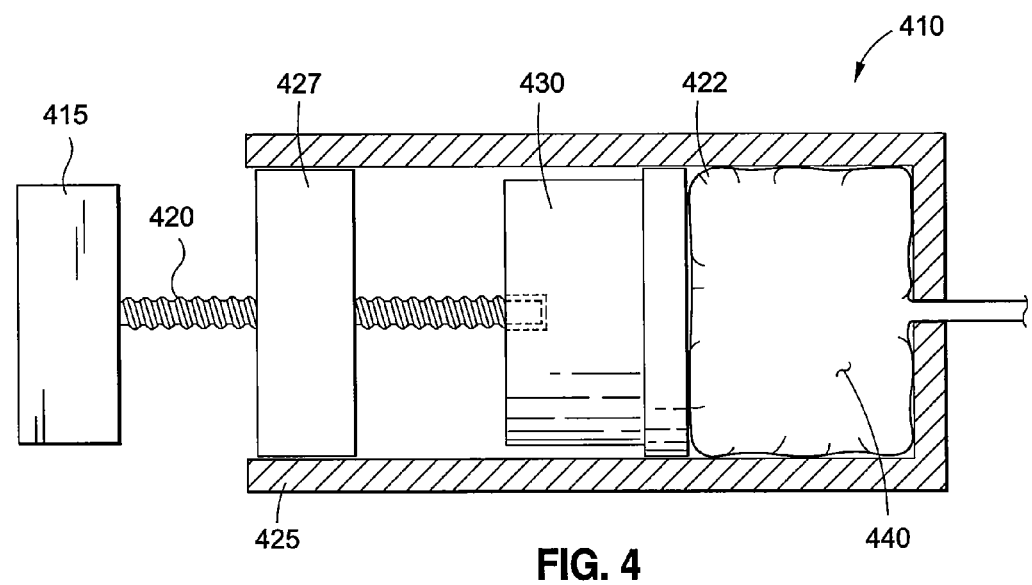
FIG. 4 illustrates a side, sectional view of an implantable pump with a flexible pouch according to an embodiment of the present invention.

In an embodiment, and with reference to FIG. 4, the fluid within the reservoir 440 may be housed within a pouch 422 or other flexible enclosure. The pouch 422 is coupled to the gastric band via tubing to facilitate inflating or deflating an inflatable portion of the gastric band. The piston 430 acts on the pouch to facilitate driving the fluid from or drawing fluid into the pouch 422. Utilizing a pouch to house the fluid reduces the need to create a seal between the piston 430 and a housing 425 of the pump 410 or the reservoir 440. Where no seal is positioned between the piston 430 and the housing 425 or the reservoir 440, a greater separation distance may exist between the piston 430 and the housing 425 such that the piston 430 may move more freely within the pump 410. In this embodiment, less friction exists between the piston 430 and the housing 425, resulting in less force being utilized to move the piston 430. Pump 410 includes internal magnet 415 connected via drive shaft 420 to header 427.

With reference again to FIG. 1, a method for adjusting the inflatable portion 103 of the gastric band 105 comprises positioning the external controller 150 proximate to or within an operating distance of a patient, the skin 109 of the patient, and/or the implantable pump 110. The external magnet 170 in the external controller 150 generates a magnetic field, and the magnetic field couples the internal magnet 115 to the external magnet 170.

As the external magnet 170 moves in a first direction (for example, rotational or linear), the internal magnet 115 also moves in the first direction. As the external magnet 170 moves in a second direction (for example, rotational or linear), the internal magnet 115 also moves in the second direction. When the internal magnet 115 moves in the first direction, the piston 130 facilitates moving a first portion of the fluid from the reservoir 140 into the inflatable portion 103 of the gastric band 105. When the internal magnet 115 moves in the second direction, the piston 130 facilitates moving a second portion of the fluid from the inflatable portion 103 of the gastric band into the reservoir 140.

Unless otherwise indicated, all numerical parameters used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the present invention are approximations, the numerical values set forth in the specific examples are reported as precisely as possible. Any numerical value, however, inherently contains certain errors necessarily resulting from the standard deviation found in their respective testing measurements.

The terms "a," "an," "the," and similar referents used in the context of describing the present invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the present invention and does not pose a limitation on the scope of the present invention otherwise claimed. No language in the specification should be construed as indicating any non-claimed element essential to the practice of the present invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, certain references have been made to patents and printed publications throughout this specification. Each of the above-cited references and printed publications are individually incorporated herein by reference in their entirety.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

In closing, it is to be understood that the embodiments of the present invention disclosed herein are illustrative of the principles of the present invention. Other modifications that may be employed are within the scope of the present invention. Thus, by way of example, but not of limitation, alternative configurations of the present invention may be utilized in accordance with the teachings herein. Accordingly, the present invention is not limited to that precisely as shown and described.

What is claimed is:

1. A system for adjusting a gastric band for treatment of obesity having an inflatable portion, the system comprising:
   a non-implantable magnet configured to produce a magnetic field;
   a non-implantable motor, coupled to the non-implantable magnet, wherein said non-implantable motor is configured to move the non-implantable magnet in a rotational direction; and an implantable device comprising:
      a reservoir containing a fluid and coupled to the inflatable portion of the gastric band;
      a magnet magnetically coupled to the non-implantable magnet, wherein the magnet is configured to rotate in response to the non-implantable magnet rotating; and
      a piston coupled to the magnet, wherein the piston is configured to move in response to the magnet rotating,
      wherein said piston is configured to apply pressure on the fluid in said reservoir and cause a portion of the fluid in the reservoir to move into the inflatable portion of the gastric band, thereby providing the system for adjusting the gastric band for the treatment of obesity.

2. The system of claim 1 wherein the implantable device further comprises a screw drive coupled between the magnet and the piston for moving the piston.

3. The system of claim 1 wherein the piston is positioned adjacent to the reservoir and decreases a volume of the reservoir by moving the portion of the fluid to the inflatable portion of the gastric band.

4. The system of claim 1 wherein the implantable device further comprises a seal disposed between the piston and the reservoir.

5. The system of claim 1 wherein the reservoir in the implantable device comprises a flexible pouch for containing the fluid.

6. The system of claim 5 wherein the pouch is coupled to the gastric band via tubing that carries the fluid from the pouch to the gastric band.

7. The system of claim 1 wherein the non-implantable magnet rotates in a first direction causing the magnet to rotate in the first direction to move the portion of the fluid out of the reservoir into the gastric band.

8. The system of claim 7 wherein the non-implantable magnet rotates in a second direction causing the magnet to rotate in the second direction to move a draining portion of the fluid out of the gastric band into the reservoir.

9. The system of claim 8 wherein the first direction is clockwise and the second direction is counter-clockwise.

10. The system of claim 1 wherein the magnet is magnetically coupled to the non-implantable magnet through the skin of a patient.

11. The system of claim 1 further comprising a flow meter coupled between the reservoir and the gastric band to measure the amount of the fluid moving into or out of the inflatable portion of the gastric band.

12. The system of claim 1 wherein the fluid is an incompressible fluid.

13. The system of claim 1 further comprising an access port fluidly coupled between the reservoir and the inflatable portion of the gastric band for filling the inflatable portion of the gastric band via a subcutaneous injection.

14. The system of claim 1 wherein the fluid is selected from a group consisting of a drug, a saline solution, and combinations thereof.

15. The system of claim 1 further comprising a slidable seal connected to the piston, wherein the slidable seal maintains a seal with a housing of the implantable device as the piston moves within the implantable device.

16. The system of claim 1 wherein the piston does not include a seal.

17. A system for adjusting a gastric band for treatment of obesity having an inflatable portion, the system comprising:
   a non-implantable magnet configured to produce a magnetic field;
   a non-implantable motor, coupled to the non-implantable magnet, wherein said non-implantable motor is configured for moving the non-implantable magnet in a rotational direction; and
   an implantable device comprising:
      a volumetrically adjustable reservoir containing a fluid and coupled to the inflatable portion of the gastric band;
      a magnet magnetically coupled to the non-implantable magnet, wherein the magnet is configured to rotate in response to the non-implantable magnet rotating; and
      a piston coupled to the magnet, wherein the piston is configured to move in response to the magnet rotation,
      wherein movement of said piston is configured to adjust the volume of the reservoir and displace a portion of the fluid in the reservoir to the inflatable portion of the gastric band.

18. The system according to claim 1, wherein the non-implantable magnet, the magnet of the implantable device, and the piston are coaxially aligned.

* * * * *